United States Patent [19]

Parodi et al.

[11] Patent Number: 5,288,833

[45] Date of Patent: Feb. 22, 1994

[54] LIQUID CATALYSTS FOR RAPID POLYMERIZATION OF LIQUID COMPOSITIONS BASES ON POLYISOCYANATES AND EPOXIDES

[75] Inventors: Fabrizio Parodi, Genova; Carlo Belgiovine, Quiliano; Carla Zannoni, Milan, all of Italy

[73] Assignee: Istituto Guido Donegani S.p.A., Novara, Italy

[21] Appl. No.: 886,599

[22] Filed: May 20, 1992

[30] Foreign Application Priority Data

May 22, 1991 [IT] Italy .................. MI 91 A/001412

[51] Int. Cl.$^5$ .............................................. C08G 18/18
[52] U.S. Cl. ........................................ 528/49; 528/73; 521/118; 521/156; 564/503; 548/229; 502/172
[58] Field of Search ............... 564/503; 528/49, 73; 521/118, 156; 548/229; 502/172

[56] References Cited

U.S. PATENT DOCUMENTS

| | | | |
|---|---|---|---|
| 3,272,712 | 9/1966 | Kalopissis et al. | 548/573 |
| 3,397,227 | 8/1968 | Sobolev | 560/209 |
| 3,624,082 | 11/1971 | Skokie et al. | 548/574 |
| 3,636,114 | 1/1972 | Tobler et al. | 564/503 |
| 3,687,897 | 8/1972 | Clarke | 528/51 |
| 3,721,650 | 3/1973 | D'Alelio | 528/51 |
| 4,562,227 | 12/1985 | Rogler et al. | 524/786 |
| 4,564,651 | 1/1986 | Markert et al. | 427/116 |
| 4,582,723 | 4/1986 | Markert et al. | 427/116 |
| 4,631,306 | 12/1986 | Markert et al. | 523/457 |
| 4,728,676 | 3/1988 | Muller et al. | 521/107 |
| 4,742,142 | 5/1988 | Shimizu et al. | 528/15 |
| 5,145,880 | 9/1992 | Parodi et al. | 521/115 |

FOREIGN PATENT DOCUMENTS

| | | |
|---|---|---|
| 0454207 | 10/1991 | European Pat. Off. . |
| 1390534 | 4/1975 | United Kingdom . |

OTHER PUBLICATIONS

Frank C. Robertson, Resin Transfer Moulding of Aerospace Resins—A Review, British Polymer Journal 20, (1988) pp. 417-429.

*Primary Examiner*—John Kight, III
*Assistant Examiner*—Rachel Johnson
*Attorney, Agent, or Firm*—George P. Hoare, Jr.

[57] ABSTRACT

The present invention relates to quaternary $\beta$-hydroxy-alkyl-ammonium halides and quaternary $\beta$-hydroxy-cycloalkylammonium halides, which are liquid at temperatures lower than 60° C., are easily and rapidly miscible in liquid epoxies, as well as in liquid poly-isocianates, generating liquid compositions which spontaneously polymerize, with fast polymerization rate, already at temperatures comprised within the range of from 0° C. to 60° C., yielding a solid, insoluble polymeric material endowed with very high values of softening temperature.

11 Claims, No Drawings

LIQUID CATALYSTS FOR RAPID POLYMERIZATION OF LIQUID COMPOSITIONS BASES ON POLYISOCYANATES AND EPOXIDES

The present invention relates to catalysts for the polymerization of mixtures of organic polyisocyanates and epoxides. More particularly, the present invention relates to catalysts which are liquid at temperatures lower than 60° C., which, when mixed with poly-isocyanates and epoxides, generate reactive liquid compositions which polymerize, spontaneously and rapidly, already at room temperature.

In the sector of thermosetting resins, polymeric products containing such isocyanurate chemical structures, which can be obtained by means of the polymerization of poly-isocyanates, as well as polymeric products containing such structures as 2-oxazolidone or, jointly, isocyanurate and 2-oxazolidone, obtainable in their turn by polymerizing mixtures of polyisocyanates with monoepoxides or poly-epoxides, claim interest in the industrial field thanks to their temperature stability, hydrolysis resistance and high values of glass transition temperature which the presence of said isocyanurate and 2-oxazolidone structures supplies to them.

Such a kind of polymeric products can hence find useful applications for manufacturing finished articles, providing surface coatings, or also manufacturing adhesives and sealants for which good chemical stability at high temperatures and/or in the presence of aggressive hydrolytic media, as well as high values of softening temperature and reduced high-temperature deformability, are required.

It is known as well, that the polymerization of liquid mixtures of di-isocyanates or poly-isocyanates and mono-epoxides or poly-epoxides can be promoted by using tertiary amines, quaternary ammonium salts, or tetra-alkyl-phosphonium halides: reference is made, e.g., to German patents 3,323,084; 3,323,122; 3,323,123; 3,323,153; 3,600,767; or, also, U.S. Pat. Nos. 3,687,897 and 4,742,142.

According to such patents, and still other patents, the polymerization of mixtures comprising polyisocyanates, poly-epoxides and a suitable catalyst is accomplished, with consequent gelation and hardening, by heating at temperature comprised within the range of from 60° C. to 150° C. and, preferably, comprised within the range of from 80° C. to 130° C.

The polymerization is subsequently completed by keeping the solidified material at temperatures higher than 150° C.

Unfortunately, the compositions known from the prior art, and therefore the finished articles which can be obtained from them, are not completely free from some drawbacks, in particular associated with the used catalytic systems. Among other, may we remind here:
Fast polymerization rates are only possible at considerably high temperatures, or in the presence of high catalyst concentrations;
The tertiary amines can be deactivated by the contact with atmospheric air due to absorption of atmospheric carbon dioxide;
Difficulties may be met in dissolving the quaternary ammonium or phosphonium salts known from technical literature, which are solid materials, which may also melt at high temperatures and generally are not very much soluble in organic solvents and resins.

For example, in U.S. Pat. No. 3,721,650, a process for polymerizing polyisocyanates with polyepoxides is disclosed, in which as the catalyst, a quaternary ammonium or phosphonium halide containing at least two hydroxyalkyl groups, is used. The presence of at least two alcoholic functions is deemed to be essential, in that the inventors wish that the catalyst becomes a part of the polymeric structure, by copolymerization with the polyisocyanate and/or the poyepoxide. In any case, these are solid catalysts, which are preferably dissolved in the other components with the aid of a solvent. Furthermore, they do not make it possible the polymerization of isocyanate/epoxide mixture to take place at temperatures close to room temperature. In fact, the data reported in above said patent, which relate to polymerization processes carried out at 70° C., indicate a certain increase in viscosity only after 30 minutes from the addition of the catalyst, and demonstrate that a solid polymeric product is only obtained after 6–12 hours. Therefore, such catalysts result to be useless for all those industrial processes in which a complete and rapid dissolution of the various components in the liquid state, as well as high polymerization rates also at room temperature, are required.

In fact, it is well-known that, as regards the methods for manufacturing articles from polymeric materials obtained by means of the polymerization of thermosetting resins, above all, in composite materials which can be obtained by means of the polymerization of thermosetting resins inside which reinforcing fibres and/or mineral powders are distributed or dispersed, the feasibility of processes based on the rapid forced mixing of liquid reactants, catalysts and, possibly, several additives; injection or suction of the resulting reactive composition into a closed mould which may, or may not, contain reinforcing fibres arranged in various configurations or patterns; sudden gelation and solidification of the composition inside the mould; and then rapid demoulding of the solid articles, is regarded as considerably interesting.

Such a type of processes are known to those skilled in the art and among them, those identified, at the international level, with the Anglo-Saxon designations "Resin Transfer Moulding", "High Speed Resin Transfer Moulding", "Resin Injection Mouldin", "Liquid Injection Moulding", "Reaction Injection Moulding", and the like, can be cited here for exemplifying purposes. Still for exemplifying purposes, reference may be made to the following paper: "Resin Transfer Moulding of Aerospace Resins—A Review", by F. C. Robertson, british Polymer Journal, vol. 20, pages 417–429 (1988).

Processes of the above type make it possible finished articles of even large size to be manufactured by means of a fast, automated and cheap manufacturing process, with a good control of the dimensions, of the thicknesses and of the structure of said manufactured articles, thanks to the constraints constituted by the precise and fixed dimensions of the hollows of the forming moulds; and by the nature, amount and geometrical arrangement—which can be predetermined with exactness and reproducibility—of the resins, fibres and/or mineral additives charged to said moulds. The suitable thermosetting resins for such processes should be characterized by very short overall gelation and setting times, anyway of the order of minutes, or, at maximum, of a few tens of minutes, in order to enable the solidified articles to be handled, and hence demoulded, after a short moulding time; such a feature would allow short mould occupancy times to be attained, and the moulds to be rapidly re-used for a further forming operation. The chemical process of polymerization of the material already turned into a solid inside the mould can be in fact completed at a later time, at high temperature, out of the mould. The acceleration of the chemical processes of gelation and hardening can be carried out by means of a strong heating of the thermosetting resin, or by adding high concentrations of catalysts, or, better, very active catalysts.

An important limitation to the use of the fast manufacturing processes of the above type results from the well-known strong exotherm, typical for the processes of polymerization of the thermosetting resins in general. A strong heating of the resin, carried out for the purpose of suitably accelerating the gelation and hardening thereof, followed by the further increase in temperature caused by the exothermic character typical of the chemical polymerization process, tends to cause a considerable overheating of the material, with possibility that a thermal decomposition may occur of the same polymeric material; of the additives contained in it, such as, e.g., mould-release agents or dispersants; as well as of cores embedded inside it, up to the vapourization of components of the materials, with foams or hollows being formed. The limitation resulting from such a overheating is furthermore particularly difficult to be overcome, because the reaction heat is difficult to be removed from the outside, owing to the rapidity of the chemical process and hence of its proceeding.

Similar considerations are true for reactive compositions capable of turning into polymeric products through fast polymerization processes, and which are suitable for the production of finished articles by means of casting processes into open moulds, or processes of spreading on shaped bodies, for accomplishing coatings of surfaces, or as adhesives or sealants, in particular when applied as layers with rather high thicknesses. Also in these cases, the application of high temperatures, such as to cause the material to get rapidly gelled and hardened, or a long-time heating before the material has turned into a solid, or, still, an overheating deriving from the exothermic character of the chemical polymerization process, may cause the same polymeric material, additives contained in it, as well as bodies or surfaces into contact with it to undergo thermal decomposition, or also cause—in particular when the material is still in the liquid or plastic state and if it shows free surfaces into contact with the atmosphere—emissions of flammable, toxic or anyway noxious vapours of chemicals into the working environment. The present Applicant has found now a novel class of liquid catalysts, consituted by quaternary β-hydroxyalkyl-ammonium halides and quaternary β-hydroxycycloalkyl-ammonium halides, which made it possible the above cited drawbacks to be overcome. These are, in fact, products which are liquid at temperatures lower than 60° C. and are easily and rapidly miscible both in liquid epoxides and in liquid poly-isocyanates, with which they generate reactive compositions which undergo rapid and spontaneous polymerization already at temperatures comprised within the range of from 0° C. to 60° C., forming a solid, insoluble polymeric material endowed with a very high value of softening temperature.

Therefore, a first object of the present invention are the quaternary β-hydroxy-alkyl-ammonium halides and quaternary β-hydroxy-cycloalkylammonium halides of formula:

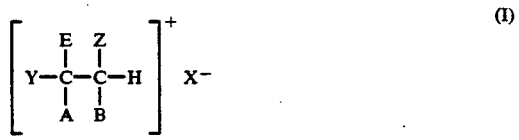

wherein:

A and B, different from each other, are —OH or an $-N^+R_1R_2R_3$ moiety, wherein $R_1$, $R_2$ and $R_3$, which may be the same, or different from one another, are $C_1$–$C_{24}$ alkyl radicals, $C_3$–$C_{14}$ cycloalkyl radicals, $C_6$–$C_{14}$ aromatic radicals, or $C_4$–$C_{24}$ radicals of mixed alkyl, cycloalkyl and/or aromatic character, optionally containing one or more functional groups selected from among ether group, olefinic double bond and acetylenic triple bond, and $R_2$ and $R_3$, taken jointly, can also constitute, together with the quaternary nitrogen atom, a heterocyclic structure;

E and Z, which may be the same, or different, from one another, are H or $C_1$–$C_{24}$ alkyl radicals, $C_3$–$C_{12}$ cycloalkyl radicals, $C_6$–$C_{14}$ aromatic radicals, or $C_4$–$C_{24}$ radicals of mixed alkyl, cycloalkyl and/or aromatic character, optionally containing one or more functional groups selected from among ether group, olefinic double bond and acetylenic triple bond, wherein Z can also be replaced by a simple covalent bond with the Y moiety;

Y is a $C_1$–$C_{50}$ alkyl radical, a $C_3$–$C_{36}$ cycloalkyl radical, a $C_6$–$C_{14}$ aromatic radical, a $C_2$–$C_{14}$ heterocyclic radical with heteroatoms being selected from among O, N, S and P, or a $C_4$–$C_{50}$ radical of mixed alkyl, aromatic and/or cycloalkyl character, optionally containing one or more functional groups selected from among ether, thioether, ester, carbonate, amido group, olefinic double bond and acetylenic triple bond, $X^-$ is a halide ion, selected from $Cl^-$, $Br^-$ and $I^-$.

A second object of the present invention is constituted by the catalysts of formula (I), which are liquid at temperatures lower than 60° C., which enable the rapid polymerization of liquid mixtures of polyisocyanates and epoxides to be carried out starting from temperatures lower than 60° C.

A further object of the present invention is constituted by the liquid reactive compositions, rapidly polymerizing starting from temperatures lower than 60° C., which comprise:

(A) at least one organic polyisocyanate;
(B) a monoepoxide or polyepoxide, or a mixture of different mono- and/or polyepoxides;
(C) at least one catalyst which is liquid at temperatures lower than 60° C., selected from among β-hydroxyalkyl-ammonium halides and β-hydroxy-cycloalkylammonium halides, corresponding to formula (I).

In the general formula (I), $R_1$, $R_2$ and $R_3$ preferably are $C_1$–$C_{18}$ alkyl radicals, $C_5$–$C_{10}$ cycloalkyl radicals, $C_6$–$C_{10}$ aromatic radicals, or $C_6$–$C_{10}$ radicals of mixed alkyl, cycloalkyl and/or aromatic character. E and Z preferably are $C_1$–$C_{18}$ alkyl radicals, $C_5$–$C_{10}$ cycloalkyl radicals, $C_6$–$C_{10}$ aromatic radicals, or $C_6$–$C_{14}$ radicals of mixed alkyl, cycloalkyl and/or aro-matic character; still more preferably, E and Z are H. Y preferably is a $C_1$–$C_{36}$ alkyl radical, a $C_5$–$C_{14}$ cycloalkyl radical, a $C_6$–$C_{10}$ aromatic radical, a $C_3$–$C_{12}$ heterocyclic radical in which the heteroatoms are selected from among O, N, S and P, or a $C_4$–$C_{36}$ radical of mixed alkyl, aromatic and/or cycloalkyl character. Y preferably contains from 1 to 6 ether groups along its chain. $X^-$ preferably is either $I^-$ or $Br^-$.

As stated hereinabove, the catalysts of the present invention are liquid at temperatures lower than 60° C. and preferably lower than 20° C., as well as perfectly soluble and easily dissolved, at temperatures lower than 60° C., in components (A) or (B) of the above composition, and preferably in both of them, or anyway in their mixtures.

Furthermore, such catalysts display the additional advantage that they do not promote early chemical reactions of polymerization of the individual components (A) and (B) within relatively long times at temperatures not higher than 60° C. Therefore, the catalysts can be preliminarily dissolved in component (A) or in component (B), and the resulting mixtures are stable and storage resistant at temperatures not higher than 60° C., for long enough times, with said mixtures being subsequently useable.

Following the polymerization process promoted by the same catalysts and possibly completed at high temperature, the liquid, reactive compositions according to the present invention turn into solid, stiff materials with a high softening temperature, generally comprised within the range of from about 150° C. to about 300° C.

Such liquid, reactive compositions can additionally contain a fourth component, which is selected from among additives and/or auxiliaries well known in the art, such as mineral fillers, short or ground fibres, pigments, extenders, stabilizers, flame-retardant agents, agents capable of endowing the present compositions with thixotropic character, lubricants, mould-release agents, antifoaming agents, propellants, foaming agents, surfactants, wetting agents and other possible known additives or auxiliaries, or associations thereof.

Both in the absence, and in association with fibres or reinforcing structures, which may also be non-fibrous, the liquid compositions as disclosed hereinabove can be used for the rapid production of finished articles, semifinished articles, surface coatings, polymeric adhesives or sealants with very high heat distorsion temperature (HDT) with an overheating of the same polymeric material, of bodies or surfaces into contact with it and/or of the additives and auxiliaries contained in it, being prevented.

Suitable organic polyisocyanates for use as component (A) in the above said compositions are those belonging to the family of compound having the general formula

wherein
m is higher than 1, and preferably is comprised within the range of from 2 to 3, and
Q is an organic m-valent, preferably divalent or trivalent, radical of from 6 to 24 carbon atoms, of aliphatic, cycloaliphatic, aromatic, heterocyclic type, or of mixed aliphatic, cycloaliphatic, aromatic and/or heterocyclic type.

A large number of disocyanates of such a type have been reported in the past, e.g., in the chapter "Diisocyanates" by A. A. R. Sayigh, H. Ulrich and W. J. Farissey Jr., in "Condensation Monomers", edited by J. K. Stille and T. W. Campbell, published by Wiley-Interscience, New York, 1972, pages 369–476.

The above organic radical Q may also contain heteroatoms not belonging to cyclic structures and/or several functional or bonding groups, which may contain or not contain heteroatoms, such as ether, thioeter, ester, carbonyl, sulfonyl, amido, carbodiimido, urethane, allophanate, biuret groups, olefinic double bonds, acetylenic triple bonds, and still others.

According to a preferred form of practical embodiment of the present invention, polyisocyanates which are liquid at temperatures lower than 60° C., and preferably polyisocyanates which are liquid at temperatures lower than 20° C., can be advantageously used. Also mixtures of different polyisocyanates, and, among said mixtures, preferably those which are liquid at temperatures lower than 60° C., or, still more preferably, those which are liquid at temperatures lower than 20° C., can be advantageously used as well.

According to the present invention, polyisocyanates are preferably used, which are selected from the group consisting of aromatic polyisocyanates, and mixtures thereof. Said polyisocyanates and their mixtures comprise toluene-2,4-di-isocyanate and toluene-2,6-diisocyanate and their mixturess, diphenylmethane-4,4'-diisocyanate, diphenylmethane-2,4'di-isocyanate and diphenylmethane-2,2'di-isocyanate and their mixtures, naphthalene-1,5-diisocyanate, 1,4-phenylene-di-isocyanate, 3,3'-dimethyldiphenyle-4,4'-diisocyanate, diphenylether-4,4'-diisocyanate and triphenylmethane-4,4', 4''-triisocyanate. Other aromatic poly-isocyanates which can be advantageously used are those polyphenylmethylene-polyisocyanates which can be obtained by phosgenating the condensation products of aniline with formaldehyde.

Modified aromatic polyisocyanates which can be advantageously used, are the isocyanate adducts which can be obtained from the reaction of one mol of a polyol containing "p" alcoholic hydroxy groups, with "mp", and preferably "p", mols of an aromatic polyisocyanate of the above cited type, containing "m" isocyanate groups, and, in particular, with "2p", and preferably "p" mols of an aromatic diisocyanate, preferably selected from among the above cited diisocyanates, or mixtures thereof. Useable polyols are, e.g., ethylene glycol, diethylene-glycol, triethylene-glycol, tetraethylene-glycol, propylene-glycol, dipropylene-glycol, tripropylene-glycol, 1,3-butanediol and 1,4-butanediol, 1,5-pentanediol, 1,6-hexanediol, trimethyl-1,6-hexanediols, glycerol, 1,1,1-trimethylolpropane, 1,1,1-trimethylolethane and mixtures thereof. The isocyanate adducts, or mixtures of several isocyanate adducts, of the above type, or mixtures of such adducts with aromatic poly-isocyanates of the above cited type, which are liquid at temperatures lower than 60° C., or, still better, at temperatures lower than 20° C., are preferably used. Examples of such isocyanate adducts which can be advantageously used, are those adducts which are liquid at room temperature, derived from aromatic isocyanates which are solid at room temperature, such as those adducts which can be obtained from the reaction of diphenylmethane-4,4'-diisocyanate with dipropylene-glycol or triethylene-glycol.

Other aromatic polyisocyanates which can be advantageously used, are the isocyanic prepolymers which can be obtained from the reaction of an aromatic polyisocyanate—selected from among those as defined hereinabove—or a mixture of a plurality thereof, with a polymeric polyol having an average molecular weight preferably comprised within the range of from 200 to 15.000. Such isocyanic prepolymers can be obtained by reacting such amounts of aromatic polyisocyanate and of said polyol, that the molar ratio of isocyanate groups to alcoholic hydroxy groups is equal to 2, or higher. Suitable polymeric polyols are polyalkylene-ether-diols such as, e.g., polyethylene-glycol, polypropylene-glycol, polytetramethylene-glycol, polyhexamethylene-glycol and the corresponding mixed polyalkylene-ether-diols.

Still other suitable polymericpolyols are those which can be obtained by mono- or poly-oxyalkenylation of different, non-polymeric polyols, with alkylene oxides, such as ethylene oxide, propylene oxide, tetrahydrofuran, isobutylene oxide or mixtures thereof, and examples of said polymeric polyols are polypropoxylated 1,1,1-trimethylolpropane, monopropoxylated or polypropoxylated glycerol, polypropoxylated sorbitol, polypropoxylated pentaerythritol. Still other polymeric polyols which can be used are the polyesters containing 2, or more, alcoholic hydroxy groups at their chain ends, and an average molecular weight preferably comprised within the range of from 400 to 10.000, such as, e.g., those which can be obtained by means of the polycondensation of a polycarboxylic acid or a mixture of several polycarboxylic acids, preferably dicarboxylic acids, with a polyol, or a mixture of several polyols, and preferably diols, so that the ratio of equivalents of alcoholic hydroxy groups to carboxylic groups is higher than 1. Suitable polyhydroxy-functional polyesters are also those, which can be analogously obtained by starting from suitable mixtures of polyols and hydroxycarboxylic acids, or from mixtures of polyols, hydroxycarboxylic acids and polycarboxylic acids, and preferably those which can be obtained from diols, monohydroxy-monocarboxylic acids and dicarboxylic acids. Other analogous polyols are, as well, polyhydroxy-functional polyesters and preferably polyester-diols and polyester-triols, which can be obtained by means of the polymerization of lactones such as, e.g., $\epsilon$-butyrolactone, $\epsilon$-caprolactone or still others, or mixtures thereof, which polymerization is initiated by means of a suitable amount of a non-polymeric polyol, and preferably a diol or triol.

Still further polymeric polyols suitable for preparing isocyanic prepolymers comprise other polymers, generally containing 2 alcoholic hydroxy groups, or more, such as, e.g., polybutadienes or polyisoprenes or butadiene/isoprene copolymers with side- and/or chain-end-alcoholic hydroxy groups, as well as polymers which can be obtained by means of the copolymerization of vinyl compounds, such as acrylonitrile, vinyl chloride, styrene and still others, either as single compounds or mixed with one another, with at least one vinyl compound containing an alcoholic hydroxy group, such as a hydroxyalkyl acrylate or methacrylate, a hydroxy-alkyl-styrene, and still others.

According to the present invention, in general aromatic polyisocyanates available from the market should be preferably used, which are commonly available, can be easily obtained, and are liquid at temperatures not higher than 40° C. or, better, not higher than 50° C. Isocyanates of such a type are, e.g., toluene-2,4-diisocyanate and toluene-2,6-diisocyanate and mixtures of such isomers and, among them, in particular, the mixture of both 2,4- and 2,6-isomers as cited above, in the ratio of 80:20, which is currently available from the market; diphenyl-methane-4,4'-diisocyanate (or "MDI"), and the mixtures thereof with the corresponding isomers diphenylmethane-2,4'-di-isocyanate, and also diphenylmethane-2,2'-diisocyanate. Aromatic polyisocyanates available from the market, of the above type, and the use of which is particularly advantageous according to the present invention, are also those products which can be obtained by means of the phosgenation of the aromatic polyamines deriving from the condensation of aniline with formaldehyde in various ratios to each other, and according to different condensation processes.

The isocyanates which can be obtained in that way, and which are commonly designated "crude MDI", are constituted by more or less complex mixtures prevailingly comprising diphenylmethane-4,4'-diisocyanate and diphenylmethane-2,4'-diisocyanate together with other isomers thereof, and various polyphenylmethylene-polyisocyanates in variable mutual ratios. Such a type of mixtures can additionally comprise isocyanates containing carbodiimide groups deriving from condensations between said isocyanates, as well as/or isocyanic adducts of said carbodiimidic compounds with said isocyanates.

Other polyisocyanates which can be used with particular advantages, are also the various mixtures consisting of diphenyl-methane-2,4'-diisocyanate and diphenylmethane-4,4'-diisocyanate which can be obtained by means of the distillation of the above cited phosgenation products, as well as the same residues from the same distillation, which are particularly rich in polyphenylmethylene-polyisocianates.

The residues of distillation can be used as well, which are constituted by complex mixtures of isocyanate group containing compounds, which can be recovered from the preparation of the commercial aromatic diisocyanates and polyisocyanates in general, and different from the polyisocyanates indicated hereinabove belonging to the family of diphenylmethane such as, e.g., the residues from distillation of toluene-diisocyanate and of other aromatic polyisocyanates selected from the families cited hereinabove.

The component (B) making up part of the reactive composition of the present invention is constituted by a monoepoxide or, preferably, a polyepoxide, or a mixture of different mono-epoxides and/or polyepoxides. Said epoxides are organic aliphatic, cycloaliphatic, aromatic, heterocyclic compounds, or compounds with mixed structure, at the ends of whose molecule epoxy groups are present in a number equal to, or higher than, 1, and preferably equal to, or higher than, 2. A large number of diepoxides and polyepoxides of said type are listed, e.g., in following references:

(a) "Handbook of Epoxy resins", by H. Lee and K. Neville, McGraw-Hill, N.Y., 1967 (or anastatic reprint of 1982), pages from 4-36 to 4-70; and (b) "Epoxy resins. New Results and Developments", by F. Lohse, Die Makromolekülare Chemie, Macromolecular Symposia, vol. 7, pages 1–16 (1987).

The diepoxides and polyepoxides which can be used comprise the polyglycidylethers of bisphenols and multivalent phenols, such as 2,2-bis-(4-hydroxyphenyl)propane ("bisphenol A"), 4,4'-di-hydroxydiphenyl-methane ("bisphenol F") and its isomers, 4,4'-dihydroxy-diphenyl-ether, 4,4'-dihydroxy-phenyl-sulfone ("bisphenol S"), hydroquinone and those hydroquinones which contain various substituents on their benzene ring, resorcinol, pyrocatechol, phloroglucinol, methyl-phloroglucinol, 1,1,3-tris-(4-hydroxyphenyl)-propane, tris-(4-hydroxyphenyl)-methane, 2,2',4,4'-tetrahydroxy-biphenyl, chlorinated or brominated bisphenols, such as 2,2-bis-(4-hydroxy-3,5-dichlorophenyl)-propane ("tetrachlorobisphenol A") and 2,2-bis-(4-hydroxy-3,5-dibromophenyl)-propane ("tetrabromobisphenol A"), as well as the polyglycidylethers of novolacs, which can be obtained by means of the polycondensation, in particular acid-catalysed polycondensation, of phenols with aldehydes, such as phenol-formaldehyde and orthocresol-formaldehyde novolacs.

Other polyepoxides which can be used comprise the polyglycidylesters of polycarboxylic acids of aliphatic, cycloaliphatic, aromatic character, and with mixed structure, such as adipic acid, linoleic acid dimer or trimer, hexahydrophthalic acid, methyl-hexahydrophthalic acid, 1,4-cyclohexane-dioic acid, phthalic acid, isophthalic acid, as well as the polyglycidylesters of polycarboxylic acids which can be obtained by means of the reaction of 1 mol of a polyol containing "n" hydroxy groups, with "n" mols of a cycloaliphatic or aromatic anhydride, such as, e.g., those deriving from 1 mol of 1,4-cyclohexanediol and 2 mols of hexahydrophthalic anhydride, from 1 mol of 1,1,1-trimethylolpropane and 3 mols of hexahydrophtalic anhydride, from 1 mol of pentaerythritol and 4 mols of hexahydrophthalic anhydride, as well as the polyglycidyl-(ether-esters) of hydroxycarboxylic acids, such as 4,4-bis-(4-hydroxyphenyl)-valeric acid. Useable polyepoxides are also those which can be obtained by means of the N-alkylation of aromatic amines, or N-alkylation and etherification of aminophenols, with epichlorohydrin. Such a type of polyepoxides include N,N-diglycidyl-aniline, N,N,N',N'-tetraglycidyl-4,4'-diamino-diphenylmethane, N,N,N',N'-tetraglycidyl-4,4'-diaminodiphenyl-sulfone, N,N-diglycidyl-4-glycidoxy-aniline. Furthermore, N-glycidylamides can be used, such as, e.g., N,N'-diglycidyloxamide, as well as several polyepoxides containing heterocyclic structures, such as triglycidyl-isocyanurate, 1,2,4-triglycidyl-1,2,4-triazoline-dione, polyglycidyl-1,3-bis-(3-hydantoinyl)-2-hydroxy-propane, as well as poly-(2-alkyl-glycidyl)ethers, and in particular, poly-(2-methyl-glycidyl)ethers, of bisphenols and multivalent phenols, such as the bis-(2-methyl-glycidyl)-ether of bisphenol A. Polyepoxides which can be used are also those which can be obtained, for example, from the reaction of a diepoxide with a bisphenol, in a variable mutual molar ratio of diepoxide/bisphenol higher than 1 and not higher than 2, and having increasing values of average molecular weight and epoxy equivalent weight as said ratio, of the amounts—as mols—of diepoxide to bisphenol supplied to the reaction, decreases from 2 towards a value of 1.

Such a type of diepoxides comprise the "higher homologues" of the diglycidylether of bisphenol A, having the chemical structure:

sponding diepoxides, which are the "higher homologues" of bisphenol F diglycidylether.

Other polyepoxides which can be used are the polyglycidylethers of such polyols as 1,4-butanediol, 1,6-hexanediol, neopentylglycol, 1,4-dimethylol-cyclohexane, 2,2-bis-(4-hydroxycyclohexyl)-propane ("hydrogenated bisphenol A"), polypropylene glycol, glycerol, 1,1,1-trimethylolpropane, pentaerythritol, castor oil.

Those polyepoxides can be used as well, which can be obtained by polyepoxidation, e.g., with peracids, of compounds containing 2, or more, olefinic double bonds, such as butadiene, 1,5-cyclooctadiene, 1,5,9-cyclododecatriene, bicyclopentadiene, 3-vinyl-cyclohexene, divinylbenzene, 4,4'-diallyldiphenylether, 2,2-bis-(4-allyl-cyclohexyl)-propane, poly-unsaturated olefins containing 2, or more, cyclohexene rings or cyclopentene rings linked by simple or multiple bridges of atoms, such as bis-(2-cyclopentenyl)-ether, 2-(3-cyclohexenyl)-5,5-spiro-cyclohex-3-ene metadioxane, 3-cyclohexenylmethyl-3-cyclohexenoate, bis-(3-cyclohexenylmethyl) adipate, esters of polyols with unsaturated carboxylic acids, such as many vegetable oils, polymers and copolymers containing double bonds of olefinic character, such as polybutadiene, polyisoprene and their copolymers with other vinylic monomers, such as styrene, as well as unsaturated polyesters. Also polymers containing epoxy groups, which can be obtained from vinyl-glycidyl monomers, such as glycidyl acrylate, glicidyl methacrylate, allyl-glycidyl ether and their copolymers with other vinylic monomers, such as styrene, α-methyl-styrene, vinyl acetate, alkyl acrylates and methacrylates, can be used.

Similarly to as already stated for polyisocyanates, according to a preferred form of practical embodiment of the present invention, polyepoxides can be used advantageously, which are liquid at temperatures lower than 60° C., and preferably are liquid at temperatures lower than 20° C. Mixtures of different polyepoxides and, among said mixtures, preferably those mixtures which are liquid at temperatures lower than 60° C., or, still better, which are liquid at temperatures lower than 20° C., can be advantageously used as well.

According to the present invention, also monoepoxides, preferably those monoepoxides which are liquid at room temperatures, and preferably as mixtures with polyepoxides of the types mentioned up to here, can be used. Said monoepoxides include the glycidylethers of such alcohols as butanol, heptanol, octanol, 2-ethyl-hexanol, allylic alcohol, as well as the glycidyl ethers of such phenols as phenol, paracresol, para-tert.-butyl-phenol, nonylphenol. The catalyst according to the present invention can be prepared by means of the reaction of a monoepoxide, or of a mixture of several monoepoxides, with a suitable amount of a secondary monoaminic compound having the formula

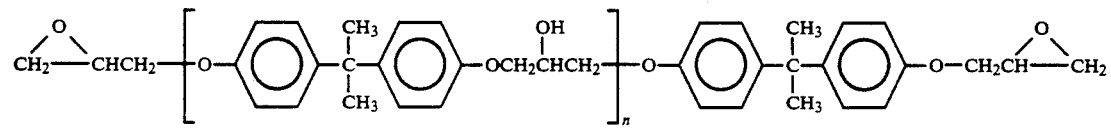

and mixtures of a plurality of them, available from the market with an average "n" value comprised within the range of from about 0.2 to about 30, as well as the corre-

R₂R₃NH, or of a mixture of secondary monoaminic compounds of said type, followed by quaternization of the tertiary β-hydroxy-aminic groups resulting from the reaction of addition of equimolar amounts of epoxy groups and aminic $R_2R_3NH$ compound, with an alkyl halide of formula $R_1X$, or with a mixture of several alkyl halides falling within the scope of that formula.

The same monoepoxides which are cited hereinabove among the constituents of component (B) are suitable for use for preparing such catalysts, and, among them, those monoepoxides are preferably and advantageously used, which are low-viscosity liquids at temperatures lower than 60° C., or, still better, at temperatures lower than 20° C.

Such a type of monoepoxides are preferably selected from the group consisting of monoglycidyl ethers of alcohols and phenols, as well as of monoglycidyl esters of carboxylic, sulfonic, phosphonic acids, and still others. Examples of such monoepoxides are: the methyl-glycidyl-ether, ethyl-glycidyl-ether, propyl-glycidyl-ether, isopropyl-glycidyl-ether, butyl-glycidyl-ether, hexyl-glycidyl-ether, 2-ethylhexyl-glycidyl-ether, allyl-glycidyl-ether, phenyl-glycidyl-ether, the methyl-phenyl-glycidyl-ethers, α- and β-naphthyl-glycidyl-ether, the nonyl-phenyl-glycidyl-ethers, para-cresyl-glycidyl-ether, para-tert.-butyl-phenyl-glycidyl-ether, glycidyl butyrate, glycidyl (meth)acrylate, glycidyl-2-ethylhexanoate, glycidyl tosilate. Propylene oxide can be advantageously used as well.

A still other monoepoxides which can be used in order to prepare the catalysts according to the present invention, include those products which can be obtained by means of the mono-epoxidation of compounds containing one or more olefinic unsaturations. Monoepoxides belonging to such a class of compounds are, e.g.: 1,2-epoxybutane and 2,3-epoxybutane, 1-methoxy-2-methylpropylene oxide, 1,2-epoxy-5-hexene, 1,2-epoxy-hexane, 1,2-epoxy-decane, 1,2-epoxy-dodecane, 1,2-epoxy-hexadecane, 1,2-epoxy-cyclohexane, 1,2-epoxy-5-cyclooctene, 1,2-epoxy-7-octene, 1,2-epoxy-cyclododecane, 1,2-epoxy-5,9-cyclododecadiene, styrene oxide, 2,3-epoxypropylbenzene, limonene oxide, 2-carene and 3-carene oxides.

Useable are, as well, the products resulting from monoepoxidation of: mono-unsaturated and poly-unsaturated carboxylic acids, such as oleic acid, linoleic acid, linolenic acid and their derivatives, such as esters or amides; mono-unsaturated or poly-unsaturated alcohols, such as oleyl alcohol, linalool and their derivatives, such as ethers or esters; amides of carboxylic acids with mono-unsaturated or poly-unsaturated primary or secondary amines, such as allyl amine or oleyl amine.

Also suitable mixtures, which are liquid, and preferably low-viscosity liquids, at temperatures lower than 20° C., of several monoepoxides, can be used as well.

The momoepoxide, or a suitable mixture of different monoepoxides, is reacted with a compound containing a secondary amino group $R_2R_3NH$, or with a mixture of different compounds of that type, in which $R_2$ and $R_3$ may optionally make up part of a ring including the nitrogen atom of —NH— group, and having an alkyl, cycloalkyl, aromatic structure, or a mixed alkyl, cycloalkyl, and/or aromatic structure and optionally containing functional groups or linkage groups, which may contain or not heteroatoms, such as, e.g., ether groups. Said secondary monoaminic compound preferably is liquid at temperatures lower than 20° C., and preferably is selected from the group consisting of secondary alkyl, cycloalkyl and arylalkyl amines and aminoethers, as well as from the group consisting of imines and iminoethers. Aminic compounds of such a type, which can be advantageously used, include diethylamine, dipropylamine, dibutylamine, diisobutylamine, dihexylamine, di-2-ethylhexylamine, N-methyl-butyl-amine, N-ethyl-propylamine, N-ethyl-butylamine, N-methyl-cyclohexylamine, N-ethyl-cyclohexylamine, N-ethylbenzylamine, di-(2-methoxyethyl)-amine, pyrrolidine, piperidine, 4-methylpiperidine, morpholine, and mixtures thereof. The amounts of monoepoxide and of secondary monoaminic compound caused to react with each other in order to prepare the catalysts according to the present invention are such that the ratio of the epoxide groups to —NH— groups is not higher than, and preferably equal to, 1.

The tertiary aminic groups obtained from the reaction of epoxy groups with —NH— groups are then transformed into quaternary ammonium groups, by causing the product resulting from the previous reaction between monoepoxide and secondary monoaminic compound, to react with an amount of an alkyl monohalide $R_1X$, or of a mixture of different alkyl mono-halides, which is stoichiometrically equivalent to, or higher than, the amount of secondary monoaminic compound used, and, in particular, such that the molar ratio of the alkyl mono-halide to the secondary monoaminic compound is preferably comprised within the range of from 1.0 to 1.1. Said alkyl mono-halide is selected from the group consisting of aliphatic, cycloaliphatic and aryl-aliphatic mono-chlorides, mono-bromides and mono-iodides, and optionally also contains functional groups, or linkage groups selected from among ether groups, olefinic double bonds, acetylenic triple bonds. According to the present invention, alkyl monoiodides or alkyl monobromides of said type are used with particular advantages.

Alkyl mono-iodides which can be used include iodomethane, iodoethane, 1-iodopropane, 1-iodobutane, 1-iodopentane, 1-iodo-3-methyl-butane, 1-iodohexane, 1-iodoheptane, 1-iodooctane, 1-iodododecane, 1-iodohexadecane, 1-iodooctadecane, aryl iodide and mixtures thereof.

Alkyl mono-bromides which can be used include bromomethane, bromoethane, 1-bromopropane, 1-bromobutane, 1-bromopentane, 1-bromo-3-methyl-butane, 1-bromohexane, 1-bromo-heptane, 1-bromooctane, 1-bromodecane, 1-bromododecane, 1-bromotetradecane, 1-bromooctadecane, allyl bromide and crotyl bromide, 1-bromo-1-propene, and mixtures thereof. The reaction between the monoepoxide, or monoepoxide mixtures, and the secondary monoaminic compound, and the following quaternization of the resulting tertiary amino groups with the alkyl mono-halide can be carried out both by using the only reactants interested by the reaction and listed hereinabove, and with the aid of known solvents which are non-reactive, or poorly reactive, with the chemical functions contained in the reaction mixture, and subsequently easily removable by distillation. Useable solvents for preparing the catalyst comprise tetrahydrofuran, dioxane, 1,2-dimethoxyethane, di-isopropyl ether, tert.-butylmethyl ether, hexane, heptane, cyclohexane, methylcyclohexane, benzene, toluene, nitromethane, and mixtures thereof. The preparation of the catalysts according to the present reaction is advantageously carried out without using solvents, or with the aid of small solvent amounts.

For illustrative, exemplifying purposes, a suitable process preferably adopted within the scope of the present invention for the preparation of the catalyst, may take place through the following main steps:

(a) The secondary mono-aminic compound is gradually added, with stirring, to the proper mono-epoxide (or mixture of several mono-epoxides), contained, in the liquid state, or liquified by dilution with a suitable solvent or solvent mixture, in a reaction vessel, preferably previously purged with an inert, dry gas, and kept at a temperature which is preferably comprised within the range of from 0° C. to 150° C.;

(b) When the addition of the aminic compound is complete, the reaction mixture is kept stirred at a temperature comprised within the same range as specified above, for a time period which may range from 0.5 to 8 hours; any secondary aminic compound possibly unreacted is removed by submitting the reaction mixture to a distillation under atmospheric pressure, or under a preferably reduced pressure;

(c) Still with stirring, and under a flowing stream of an inert gas, the alkyl halide is added, with the temperature the reaction mixture being simultaneously kept comprised within the range of from 0° C. to 40° C.; the same mixture is then kept stirred at a temperature comprised within the same range, for a time period of from 1 to 6 hours; still with stirring, the reaction mixture is then brought up to, and kept at, a temperature preferably comprised within the range of from 50° C. to 120° C., for a time period ranging from 6 to 60 hours, and then is cooled; more in general, the reaction mixture can be also kept at a temperature within the range 40°-120° C. for a time period ranging from 6 to 100 hours, and then cooled.

(d) The solvent, if used, and any possibly unreacted alkyl halide are removed by distillation under atmospheric pressure, or under a preferably reduced pressure.

The catalysts according to the present invention can be prepared according to several other methods known from the prior art.

Such methods comprise:

(a) Quaternization of a tertiary mono-aminic compound

with halohydrins having the formula:

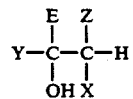

or

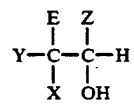

or mixtures thereof, wherein the various substituents have the respective meanings reported hereinabove. In their turn, said halohydrins can be prepared by means of methods known from the prior art, such as, e.g., addition of hydrogen halides to epoxides, or addition of hypohalogenous acids to compounds containing double bonds of olefinic character.

(b) Quaternization of tertiary alkanolamines or cycloalkanolamines of formula:

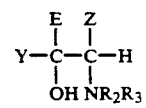

or

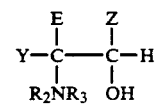

with alkyl mono-halides

wherein the various substituents have the respective meanings reported hereinabove.

Examples of liquid catalysts which can be used in the present invention, and can be prepared by means of the above disclosed processes, are reported in the following Table I.

TABLE I

| Y | E | Z | A | B | X— |
|---|---|---|---|---|---|
| $CH_3(CH_2)_3OCH_2-$ | —H | —H | —OH | —N'$(C_4H_9)_3$ | I— |
| $CH_3(CH_2)_3CHCH_2OCH_2-$<br>            \|<br>            $C_2H_5$ | —H | —H | —OH | —N'$(C_2H_5)_3$ | I— |
| $C_6H_5-O-CH_2-$ | —H | —H | —OH | —N'$(n-C_4H_9)_3$ | Br— |
| $(CH_3)_3C-C_6H_4-O-CH_2-$ | —H | —H | —OH | —N'$(C_2H_5)_2(n-C_4H_9)$ | I— |
| $CH_3(CH_2)_3-O-CH_2-$ | —H | —H | —OH | —N'$(n-C_4H_9)_3$ | Br— |
| $CH_3-$ | —H | —H | —OH | —N'$(CH_3)_2(n-C_8H_{17})$ | I— |
| $C_6H_5-$ | —H | —H | —OH | —N'$(C_2H_4OCH_3)_2(C_2H_5)$ | I— |
| $CH_3-$ | —H | —$CH_3$ | —OH | —N'$(C_2H_5)_2(n-C_8H_{17})$ | I— |
| $CH_3-$ | —$CH_3$ | —$OCH_3$ | —N'$(CH_3)_2(C_5H_{11})$ | —OH | I— |
| $CH_3-$ | —H | —H | —OH | —N'$(CH_3)_2(n-C_6H_{13})$ | Cl— |

TABLE I-continued

| Y | E | Z | A | B | X— |
|---|---|---|---|---|---|
| CH₂—<br>\|<br>CH₂   CH₂—(Z)<br>  \ /<br>   C<br>   \|<br>CH₃—C=CH₂ | —CH₃ | simple bond with Y | —N'(CH₃)₂(C₂H₅) | —OH | I— |
| CH₂—<br>\|<br>CH₂   CH₂—(Z)<br>  \ /<br>   CH₂ | —H | simple bond with Y | —OH | —N'(CH₃)₂(n-C₅H₁₁) | Br— |
| C₂H₅—OOC—(CH₂)₇— | —H | —(CH₂)₇CH₃ | —OH | —N'(C₂H₅)₂(CH₃) | I— |
| CH₂=C—COO—CH₂—<br>   \|<br>   CH₃ | —H | —H | —OH | —N'(n-C₄H₉)₂(n-C₅H₁₁) | |

The catalyst obtained in that way are, at a temperature lower than 60° C., more or less viscous liquids with a variable colour, spanning from light yellow to brown. The mixtures of components "A"/"B" are liquids preferably low-viscosity liquids, at temperatures lower than 60° C., as well as stable, in the absence of catalyst "C", over a relatively long time, at temperatures both higher than, and lower than, 60° C.

If components "A" and "B" are, per se, liquids, the catalysts according to the present invention are rapidly and completely soluble in both said components "A" and "B" of the reactive composition of the present invention and, anyway in "A"/"B" mixture, which is liquid at temperatures lower than 60° C.

Such catalysts can be used neat, or diluted with a suitable amount of a liquid mono-epoxide or poly-epoxide selected from among those as indicated hereinabove as constituents of component "B" of the reactive composition.

The component "A", constituted by a polyisocyanate, or a mixture of different polyisocyanates, and the component "B", constituted by an epoxide, or a mixture of different epoxides, as disclose hereinabove, are used to prepare the liquid reactive composition of the present invention in variable amounts, anyway such that the ratio of isocyanate groups to epoxy groups respectively supplied by said components "A" and "B", is comprised within the range of from 99:1 to 50:50, and preferably is comprised within the range of from 95:5 to 55:45.

The liquid catalyst "C" is contained in the reactive composition in amounts comprised within the range of from 0.01 to 10 parts by weight of halogen "X" per each 100 parts by weight of "A"/"B" mixture of polyisocyanates and epoxides, and preferably comprised within the range of from 0.1 to 4.

The mixture consisting of components "A" and "B" and catalyst "C", in such mutual ratios as stated hereinabove, is a reactive composition which is liquid at temperatures lower than 60° C. and preferably lower than 20° C., which already if left standing at a temperature comprised within the range of from 0° C. to 60° C., and still more rapidly if heated up to higher temperatures, spontaneously undergoes a rapid process of polymerization and gelation promoted by said catalyst "C".

Such reactive compositions can be used in order to rapidly produce finished articles, semifinished parts, surface coatings, adhesives and sealants consisting of a polymeric material with a high or very high value of softening temperature, by means of a variety of continuous or batchwise processes well-known in the technological sectors of fabrication and of the applications of thermosetting resins, and of their related composite materials, or by means of variants of said processes.

The gelation and subsequent hardening of said compositions may be caused to take place within a time which is shorter, the higher the adopted operating temperature, and the larger the amount of catalyst "C" added to the mixture of polyisocyanates and epoxides.

As already mentioned hereinabove, additives and auxiliaries, as well as associations of a plurality of them, the use of which is well-known to those skilled in the art of plastics and thermosetting resins, can be used as further components of the compositions according to the present invention. The addition of such substances is carried out in order to obtain a polymeric material endowed with special and suitable characteristics, so as to better match the material to the operations of the fabrication process used from time to time, or in order to simply reduce the cost of the same material.

Among the additives known in the art, mineral fillers, such as, e.g., China clay, talc, mica, calcium carbonate, dolomite, alumina, silica or glass powders, short glass fibres or ground fibreglass, carbon fibres, asbestos fibres, and still others, white pigment powders, such as titanium dioxide, zinc oxide, barium carbonate and barium sulfate and still others, black pigments, as carbon black, coloured pigments, lubricant powders, such as graphite powder and molybdenum disulfide powder, inorganic flame retardants, such as antimony trioxide, metal borates and metal phosphates, organic flame retardants, such as various polyhalogenated compounds, organic phosphates and organic phosphonates, can be advantageously used, either alone, or in association with one another.

Additives and auxiliaries, which can be used also in association with the preceding ones and with one another, are stabilizers, dyes, extenders, release agents, agents endowing the compositions with a thixotropic character, antifoaming agents, propellants, foaming agents, surfactants, emulsifiers, and still others, the use of which is well-known in the art.

The modalities of preparation of the liquid compositions of the present invention may be very different, according to the type of process selected in order to fabricate the finished articles, semi-finished parts, surface coatings, adhesives or sealants, from the same composition, as well as according to the intrinsic or desired gelation and hardening rate of the same composition, i.e., of the desired rate of production of said finished articles, semifinished parts, solid polymeric adhesives or sealants.

In this regard, we wish to underline that the catalysts according to the present invention offer a complete operating freedom in the selected working modalities, both by virtue of the rapid and complete solubility of said catalysts in the individual components "A" and "B", as well as in their "A"/"B" mixtures, and thanks to the good stability, also over long time periods, shown by the mixtures constituted by the catalyst and component "A" or component "B" within the temperatures range of from 0° C. to 60° C., within which the polymerization is advantageously promoted and carried out.

The liquid compositions of the present invention can be prepared according to well-known methods, by means of the simultaneous and continuous mixing of components "A" and "B" and of catalyst "C", forced to flow, in suitable mutual flow rate ratios, and to converge, getting mixed within an extremely short time interval, flowing along a suitable duct, hollow, nozzle or the like, which they are caused to continuously exit, being directly fed, by now as a homogeneous liquid mixture, to the proper duct through which the resulting composition is injected, cast, spread, or sprayed.

The compositions can alternatively be prepared in an at all analogous way, by continuously mixing the component "A" with a preliminarily prepared mixture of component "B"/catalyst "C", or by continuously mixing the component "B" with a preliminarily prepared mixture of component "A"/catalyst "C", or by continuously mixing the catalyst "C" with a preliminarily prepared mixture of component "A"/component "B".

The optional additives and auxiliaries of the composition are preferably homogeneously pre-dispersed in components "A" or "B", or in "A"/"C", "B"/"C" or "A"/"B" mixtures. In particular, if batchwise and relatively slow processes, such as, e.g., casting into moulds, are adopted, one may also prepare the reactive composition aliquot-by-aliquot, by mixing suitable amounts of all the several components in a suitable container, and subsequently use the whole aliquot of composition prepared from time to time.

Such a procedure can be applied when dealing with reactive compositions which would polymerize within long enough times, and/or adopting a mixing/handling temperature which is low enough, in order to allow the components to be perfectly homogenized and the liquid composition to be injected, cast, spread or sprayed before the gelation thereof may take place.

When mixing is complete, the reactive composition left standing at, or brought to, a temperature comprised within the range of from 0° C. to 60° C., or, optionally, higher than that, can, according to the process used, be injected, intaken, cast, extruded, spread or sprayed into different moulds, shaped hollows, or onto shaped bodies or substrates, and then is allowed to spontaneously and rapidly gel and harden. In other terms, when the composition is adjusted at a temperature comprised within the range of from 0° C. to 60° C., said composition spontaneously sets, i.e., with no need for a further heating from the outside, turning into a solid polymeric material which can be handled within a time which is preferably comprised within the range of from a few minutes, up to some ten minutes. Furthermore, such a hardening time can be even considerably reduced, by bringing the same composition to temperatures higher than 60° C. and/or adopting particularly high concentrations of catalyst "C" within the concentration range set forth hereinabove.

According to the present invention, the solid polymeric articles resulting from the spontaneous and rapid hardening of the reactive composition, and optionally containing mineral fillers, fibres and/or other known additives or auxiliaries, is subsequently advantageously submitted, also at a separate site, to a post-curing heat treatment which causes the polymerization level thereof to increase and come to completion, resulting in very high values of softening temperature, stiffness and/or tenacity, hardness and insolubility thereof.

Such a post-curing treatment of the already set reactive composition can be carried out by keeping the fabricated article at a temperature comprised within the range of from 50° C. to 250° C., and preferably of from 100° C. to 200° C., for a time period of from 0.5 to 24 hours, and preferably of from 0.5 to 6 hours.

By means of the suitable post-curing heat treatment, the polymeric material which can be obtained from the reactive composition according to the present invention can reach softening temperature values which are higher than 250° C. and generally are comprised within the range of from 150° C. to 300° C., considerably high hardness values, high values of elastic modulus, complete, or nearly complete, insolubility. Other characteristics of the polymeric material which can be obtained from the composition of the instant finding, and even in the absence of additives or auxiliaries, are a low flammability and good selfextinguishing properties, as well as high adhesive power to many substrates, such as metals, glass and ceramic materials.

The liquid reactive compositions according to the present invention can also be advantageously used for rapidly manufacturing finished articles or semi-finished parts constituted by composite polymeric materials with high heat distorsion temperatures, and reinforced by means of stiff and/or high-resistance long fibres and continuous fibres, such as fiberglass, carbon fibres, polyaramidic fibres, silicon carbide fibres, boron fibres, ceramic fibres, metal fibres or other known fibres or fibre associations, and/or with various reinforcing structures or inserts, made from metal or non-metal materials, as well as for the fast encapsulation or embedding of various kinds of parts, such as, e.g., electrical or eletronic circuits or devices, or the like.

Continuous bundles, tapes, mats, fabrics, non-woven fabrics, templates, and other aggregates of fibres and associations thereof, as well as various reinforcing fibres or inserts of metal materials or non-metal materials, or also several articles of various shapes and size, can be wetted and impregnated with the liquid reactive composition, and "embedded" inside it. The same reactive composition is then allowed to rapidly harden and is subsequently submitted to a post curing thermal treatment according to as reported hereinabove.

The liquid reactive compositions of the present invention are particularly suitable for manufacturing finished articles which may be of also large size, and/or also of high thicknesses, by means of those processes which are known with the names of "Resin Transfer Moulding", "High Speed Resin Transfer Moulding", "Liquid Injection Moulding", "Reaction Injection Moulding" and the like, or by means of variants thereof. In said processes, the composition, preferably kept, or preliminarily heated, at a temperature comprised within the range of from 0° C. to 60° C., is rapidly injected, or intaken, into a closed mould previously heated up to a temperature comprised within the same range, is let polymerize and harden inside said closed mould, with no need for heating from the outside, within a very short time interval and anyway not longer than a few ten minutes, and is subsequently and rapidly demoulded, in the form a solid manufactured article.

Inside the above said fabrication mould there can be previously arranged mats, fabrics, non-woven fabrics, templates or other aggregates of fibres and/or various reinforcing structures or inserts of metal materials or of other materials, which are impregnated and embedded by the liquid reactive composition during the injection thereof and form with it, after polymerization, a manufactured article of composite, reinforced polymeric material.

The liquid, reactive compositions of the present invention are also suitable, regardless of whether they are associated, or not, with the various reinforcing fibres or structures as indicated hereinabove, for rapidly manufacturing finished articles of semi-finished parts of polymeric material, by means of other batchwise processes known in the field of thermosetting resins. In other terms, the reactive composition can, e.g., be cast, under atmospheric pressure or under vacuum, into shaped hollows or open moulds, or spread or sprayed onto shaped bodies, or it can also be charged to a mould and, inside it, forced to match the shape thereof, by a counter-mould, or it can be applied onto a shaped hollow and then forced to match the shape thereof by an elastic, or anyway deformable, membrane forced to adhere to said shaped body by the application of a vacuum and/or compressed gas, being then allowed to polymerize and harden at such low temperatures and within such short times, as indicated hereinabove.

The same compositions can be used as well for rapid, continuous manufacture of such semi-finished parts as profiles, pipes, bars, sheets, plates, panels and the like, either containing or non-containing long or continuous reinforcing fibres or different kinds of inerts. The composition, prepared by the continuous, on-line mixing of the components thereof, can be extruded or cast in continuous mode jointly with, or without, bands, tapes, fabrics, continuous non-woven fabrics, and the like, of fibres, through variously shaped nozzles, and let rapidly polymerize and harden along the same processing line.

The compositions according to the present invention are furthermore suitable for being used for rapidly coating or painting, e.g., for protecting or decorative purposes, surfaces of various articles, as well as for rapidly glueing parts of articles, or also for rapidly sealing junctures, unions or crevices between different parts of articles. The liquid reactive composition can be prepared aliquot-by-aliquot, or, preferably, by continuous, on-line mixing of the components thereof, and then be spread, sprayed or injected, practically immediately, into/onto surfaces, junctures, unions or crevices concerned by the treatment, and let rapidly harden. In particular for use as a coating or paint, the reactive composition can comprise known extenders or solvents which may reduce the viscosity thereof, and, in particular, which can be subsequently removed by volatilization at suitable, more or less high, temperatures.

The present invention is better illustrated by the following examples, which are supplied for merely indicative, non-limitative purposes within the scope of the same invention.

EXAMPLE NO. 1

195.6 g of butyl-glycidyl ether were charged to a 5-necked glass flask of 1 liter of capacity equipped with mechanical stirring means, thermometer, reflux condenser, charging funnel and inlet fitting for dry nitrogen, which was slowly flown through the reaction mixture during the whole process which took place subsequently. To the flask, the contents of which were previously adjusted at 20°-25° C., 194.1 g of dibutylamine were then dropwise added during about 30 minutes and with good stirring, with the temperature of the mixture being kept within the range of 20°-40° C. The temperature of the reaction mixture was then increased, during a time of about 1 hour, up to 80°-85° C. and was kept within that temperature range, still with stirring, for a further time of about 6 hours, and then was cooled down to 0° C. 276.8 g of 1-iodobutane were then added dropwise during a 30-minute time, with the reaction mixture being still kept stirred. The temperature of the resulting mixture was brought, within a time period of approximately 2 hours, to 20°-25° C. After a further 2 hour stay at that temperature, the reaction mixture was gradually heated up to 90°-95° C. and was kept stirred at that temperature for about 50 hours; it was then cooled down.

The catalyst prepared in that way is, at 20°-25° C., a highly viscous liquid with a yellowish colour. A liquid reactive composition was prepared by rapidly mixing, at about 25° C.:

236.3 g of "crude" MDI polyisocyanate with a content of isocyanate groups (as determined by reaction with dibutylamine, followed by back-titration with methanolic HCL) of 30.75% by weight, and a viscosity of 131 cPs at 25° C.;

52.5 g of an epoxy resin having a chemical structure close to diglycidyl ether of bisphenol A, a value of epoxy equivalent weight (as determined by titration with hydrogen bromide according to known methods) of 178.2 and a viscosity of 8,725 cPs at 25° C.;

52.5 g of 1,4-butanediol diglycidyl ether, with a value of epoxy equivalent weight of 103.1 (as determined as described hereinabove);

8.75 g of the catalyst prepared according to the process disclosed hereinabove.

The resulting liquid composition was rapidly cast into a flat mould kept in vertical position, of aluminum, with an inner hollow of 250 mm×250 mm×4.5 mm of size, pre-heated at 50° C. After 5 minutes from the filling completion, the mould was opened and a plate of a translucid, glass-like, polymeric materials of amber colour was demoulded. The plate was subsequently conditioned in an oven for 1 hour at 100° C., 1 hour at 150° C., 2 hours at 180° C. and then 30 minutes at 200° C.

The plate, after being heat-treated in that way, and cooled down to room temperature, was cut into rectangular specimens, on which the following values of mechanical properties of the material obtained in that way were determined at 23° C. (according to ASTM D 790):

| | |
|---|---|
| - flexural elastic modulus: | 3.34 GPa; |
| - flexural strength: | 61.3 MPa. |

The polymeric material so prepared was furthermore characterized by a value of softening temperature of about 220° C. (as determined by scanning differential calorimetry).

The mechanical properties of the material as measured at the temperature of 100° C., resulted to be:

| - flexural elastic modulus: | 2.75 GPa; |
|---|---|
| - flexural strength: | 73 MPa. |

EXAMPLE NO. 2

A liquid catalyst was prepared by reacting, according to the process disclosed in Example No. 1, 200.0 g of phenyl-glycidyl ether, 163.6 g of dibutylamine and 214.8 g of 1-bromobutane. Differently from as indicated in the preparation procedure of Example No. 1, the quaternization reaction with 1-bromobutane was carried out during 100 hours at the temperature of 80°–85° C. At the end of the reaction, the excess of bromobutane was removed by reduced-pressure distillation.

A liquid reactive composition comprising the just disclosed catalyst was used for the fast preparation of a plate of fibreglass-reinforced polymeric composite material by means of a closed-mould injection process.

To two steel tanks equipped with mechanical stirring means, purged with dry nitrogen, respectively maintained at 25° C. and 60° C., and connected with an injection machine for injection moulding of thermosetting resins Venus EP 03, the following were respectively charged:
1. To the tank at 25° C., "crude" MDI of Example No. 1, in mixture in the ratio of 16.5:1 by weight, with the above disclosed catalyst;
2. To the tank at 60° C., the same epoxy resin from bisphenol A of Example No. 1.

To an aluminum mould with an inner rectangular hollow of 300 mm×300 mm×6.4 mm of size, equipped with heating/cooling coils supplied with diathermic oil circulated by means of a suitable central oil circulation unit and installed between the platens of a hydraulic press, four layers were charged of a mat of continuous glass fibers with a nominal average weight per surface unit of 450 g/m$^2$.

The liquid reactive composition was injected into the mould, pre-heated at 60° C., with the mixing/injection nozzle of the machine, which nozzle is provided with a static tubular mixer fed, under a pressure of 4 bar, with two streams, pumped from both tanks, in the mutual flow rate ratio of 70:30, respectively of the mixture of "crude" MDI and catalyst, and of the epoxy resin.

The filling of the mould was carried out during a 10 second time. after 15 minutes from the injection, the mould was opened and a solid plate of composite polymeric material was demoulded, which was submitted to a post-curing heat treatment in an oven at 120° C. for 1 hour, 150° C. for 1 hour and then 200° C. for a further 2 hours.

The plate was subsequently cut into rectangular specimens, which were used in order to determine the characteristics of the obtained material:
(a) the fiberglass content, by means of a differential weighing method, by determining the weight of some specimens before and after combustion in muffle at 600° C.; said fiberglass content was of 20.2% by weight;
(b) the softening temperature; by means of flexural dynamic mechanical analysis performed with a Dynastat Dynamic Mechanical Analyzer at a frequency of 1 Hz; the softening temperature was of approximately 260° C.;
(c) flexural elastic modulus at 23° C., according to ASTM D 790: 5.75 GPa;
(d) flexural strength at 23° C., according to ASTM D 790: 195 MPa.

It can be observed that the liquid isocyanate/catalyst precursor mixture disclosed under (1) does not show any noticeable increases in viscosity even after a 60-day long storage at 50° C. When used according to identical modalities as disclosed hereinabove, said aged precursor mixture showed an at all equivalent behaviour to the same precursor mixture, as just prepared.

EXAMPLE No. 3

A catalyst, which is a viscous liquid at 50° C., was prepared by reacting, according to the same modalities of Example No. 1, 287.2 g of 2-ethylhexyl-glycidyl ether, 112.8 g of diethylamine and 241.0 g of iodoethane. In the present case, the reaction of quaternization with iodoethane was carried out during a 50-hour time at 70°–75° C.

The resulting catalyst was used in order to promote the room-temperature polymerization of a suitable liquid reactive mixture filled with mica, and filled into cylindrical moulds by means of an injection machine for thermosetting resins Venus EP 03. The machine was connected with two steel tanks equipped with mechanical stirring means, purged with dry nitrogen, and both maintained at the room temperature of 27° C. To said tanks, the following were respectively charged:
1. A mixture, in the mutual ratio of 47:20:3 by weight, of "crude" MDI of Example No. 1, of ground and calcined mica and of the suitably prepared catalyst;
2. A mixture, in the mutual ratio of 20:30 by weight, of the same "crude" MDI and a polyfunctional polyglycidyl phenol-formaldehyde novolac epoxy resin, having an epoxy equivalent weight of 207.3.

The liquid reactive composition was prepared by feeding the mixing/injection nozzle of the machine with two streams, coming from the respective tanks 1 and 2, in the mutual ratio of 1.4:1. Such a mixture was directly injected into thin-wall, cylindrical metal moulds of 50 mm of diameter and 100 mm of height, kept in vertical position, and open atop towards the working surrounding. The hardening of the reactive composition took place spontaneously inside said cylindrical moulds after 20 minutes from their filling, with a reaction exotherm being developed, which caused the temperature of the resin at the centre of the cylinders to reach the value of approximately 150° C.

After a further time of about 10 minutes, the solid cylinders of polymeric material formed in that way were demoulded and charged to an oven at 180° C. for 2 hours, and then were allowed to cool. The resulting cylindrical bodies could be machined on the lathe and the material which constitutes them showed a softening temperature value of about 297° C.

We observe that the liquid isocyanate/catalyst precursor mixture disclosed under (1) does not show any noticeable increases in viscosity even after after a 60-day long storage at 50° C. When used according to identical modalities to as disclosed hereinabove, said aged precursor mixture showed an at all similar behaviour to the same precursor mixture, as just prepared.

EXAMPLE NO. 4

A liquid catalyst was prepared as follows.

103.0 g of N-(2-hydroxypropyl)-dimethylamine were charged to a 500 ml flask equipped as disclosed in Example 1, and dipped in a water-ice bath; with good stirring, 240.0 g of 1-iodooctane were then added dropwise, during a time interval of approximately 1 hour. The temperature of the reaction mixture was allowed to spontaneously rise, within about 4 hours, up to 20°–25° C. and then was kept at that value for a further time of approximately 12 hours. Still with stirring, the temperature of the mixture was slowly increased up to 40°–45° C. and was then kept at that temperature for about 6 hours. After cooling to room temperature, the product had the appearance of a light yellow coloured liquid, with a honey-like viscosity.

To both tanks connected with the injection-moulding machine for thermosetting resins used in Example No. 2, both maintained at 50° C., the following were respectively charged:

1. A liquid mixture of MDI isomers, of light yellow colour, with an isocyanate equivalent weight of 129.2 and prevailingly constituted by diphenylmethane-4,4'-; -2,4'-; and -2,2'-diisocyanate isomers, in the mutual ratio of 56:30:14;
2. A mixture, in the mutual ratio of 38:2 by weight, respectively of 1,6-diglycidosy-hexane and of the above disclosed catalyst.

A liquid reactive composition was prepared by feeding the mixing/injection nozzle of the machine with two streams flowing from both tanks, so as to obtain a volumetric ratio of isocyanate to diepoxide/catalyst mixture of 6:4.

The composition was directly injected into the same mould mentioned in Example No. 2, inside which three layers of fiberglass mat of 400 g/m$^2$ were preliminarily charged, and pre-heated at 50° C. The injection time was of 15 seconds.

After 8 minutes from the injection, from the mould a solid plate of composite material was extracted, and was submitted to a post-curing thermal treatment in an oven, for 1 hour at 100° C., 2 hours at 150° C. and then 1 hour at 170° C. The resulting reinforced polymeric material had a glass transition temperature, as determined by dynamic-mechanical analysis carried out with a Dynastat analyzer on rectangular specimens cut from said plate, of about 180° C.

EXAMPLE NO. 5

To both tanks connected with the Venus machine for thermosetting resin injection moulding used in Example No. 2, and both let at the room temperature of 24° C., the following were respectively charged:

1. A mixture consistited by 98 parts by weight of the same "crude" MDI as used in Example 1, and 2 parts by weight of the catalyst prepared and used in Example No. 3;
2. A mixture constituted by 57 parts by weight of 1,4-diglycidoxybutane and 43 parts by weight of triglycidyl ether of 1,1,1-trimethylopropane.

A liquid reactive composition was prepared by feeding the mixing/injection nozzle of the Venus machine of Example No. 2, with two streams pumped from the respective tanks, respectively containing the isocyanate/catalyst mixture and the polyepoxide mixture in the mutual volumetric ratio of 65:35.

The mixture was injected into the same mould described in Example No. 2, and pre-heated at 50° C. The injection time was of 10 seconds. After 6 minutes from the injection, the mould was opened and a solid plate of polymeric material was demoulded and was conditioned for 1 hour at 90° C., 1 hour at 140° C. and then 2 hours at 200° C. The so obtained material showed a Vicat softening point not lower than 250° C.

EXAMPLE NO. 6

206 g of p-tert.-butylphenyl-glycidyl ether, 101 g of N-butyl-ethylamine and 156 g of iodoethane were reacted according to the process disclosed in Example No. 3. The catalyst prepared in that way was, at 50° C., a very viscous liquid with a dark-amber colour. Such a catalyst was used as in Example 1, in lieu of the catalyst used there.

In the instant case, the mould was opened after 15 minutes of the filling and the resulting plate of polymeric material was submitted to the same thermal cycle, after which it displayed the same properties indicated in Example No. 1.

EXAMPLE NO. 7

A suitable bromohydrin for preparing a catalyst by means of a quaternization reaction with a tertiary amine was obtained as follows.

A mixture consisting of 226 g of a 33% by weight solution of HBr in anhydrous acetic acid and 100 g of glacial acetic acid was added dropwise, and with stirring, to a solution of 120 g of butyl-glycidyl ether in 200 g of glacial acetic acid in a 1-liter flask kept cooled in a water-ice bath. When the addition of HBr solution was completed, the mixture was kept at room temperature for about 4 hours and then was poured into a large volume of solution of sodium chloride in water kept at about 0° C. The liquid bromohydrin deriving from the reaction, prevailingly constituted by 1-butoxy-2-hydroxy-3-bromopropane and minor amounts of the related 2-bromo-3-hydroxy-isomer, was separated, was further washed with a little cold water, was diluted with dichloromethane, was dried over anhydrous sodium sulfate and was deprived of the same solvent by distillation.

To a flask of 500 ml of capacity, equipped as disclosed in Example No. 1, 100 g of the resulting bromohydrin were charged together with 80 g of tributylamine. The reaction mixture was kept at 100° C. for about 200 hours under nitrogen, and with strong stirring.

The resulting product, a viscous liquid at room temperature, was used as a catalyst, exactly as disclosed in Example No. 2, as a substitute for the catalyst used in that Example. The resulting reinforced polymeric material displayed the same thermal and mechanical characteristics as reported in said Example No. 2.

We claim:

1. Liquid reactive compositions, rapidly polymerizing starting from temperatures lower than 60° C., comprising:
   (A) at least one organic polyisocyanate;
   (B) a monoepoxide or polyepoxide, or a mixture of different mono-and/or polyepoxides;
   (C) at least one catalyst which is liquid at temperatures lower than 60° C., selected from among quaternary β-hydroxyalkylammonium halides or quaternary β-hydroxycycloalkylammonium halides of formula (I)

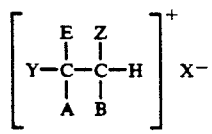

wherein:

A and B, different from each other, are —OH or an

moiety, wherein $R_1$, $R_2$ and $R_3$, which may be the same or different from one another, are $C_1$–$C_{24}$ alkyl radicals, $C_3$–$C_{14}$ cycloalkyl radicals, $C_6$–$C_{14}$ aromatic radicals, or $C_4$–$C_{24}$ radicals of mixed alkyl, cycloalkyl and/or aromatic character, optionally containing one or more functional groups selected from among ether group, olefinic double bond or acetylenic triple bond, and $R_2$ and $R_3$, taken jointly, can also constitute, together with the quaternary nitrogen atom, a heterocyclic structure;

E and Z, which may be the same or different from one another, are H or a $C_1$–$C_{24}$ alkyl radical, a $C_3$–$C_{12}$ cycloalkyl radical, a $C_6$–$C_{14}$ aromatic radical, or a $C_4$–$C_{24}$ radical of mixed alkyl, cycloalkyl and/or aromatic character, optionally containing one or more functional groups selected from among ether group, olefinic double bond or acetylenic triple bond, wherein Z can also be replaced by a simple covalent bond with the Y moiety;

Y is a $C_1$–$C_{50}$ alkyl radical, a $C_3$–$C_{36}$ cycloalkyl radical, a $C_6$–$C_{14}$ aromatic radical, a $C_2$–$C_{14}$ heterocyclic radical with heteroatoms being selected from among O, N, S or P, or a $C_4$–$C_{50}$ radical of mixed alkyl, aromatic and/or cycloalkyl character, optionally containing one or more functional groups selected from among ether, thioether, ester, carbonate, amido groups, olefinic double bond or acetylenic triple bond, and X is a halide ion, selected from $Cl^-$, $Br^-$ and $I^-$.

2. Liquid reactive compositions according to claim 1, in which the component (A) is an organic polyisocyanate, or a mixture of organic polyisocyanates of formula

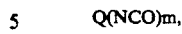

wherein m is an integer higher than 1, Q is an organic m-valent radical of aliphatic, cycloaliphatic, aromatic, heterocyclic type, or of mixed aliphatic, cycloaliphatic, aromatic and/or heterocyclic type.

3. Liquid reactive compositions according to claim 2, in which m is equal to either 2 or 3.

4. Liquid reactive compositions according to claim 2, in which Q contains from 6 to 24 carbon atoms.

5. Liquid reactive compositions according to claim 1, in which the component (A) is an aromatic polyisocyanate, or a mixture of aromatic polyisocyanates.

6. Liquid reactive compositions according to claim 1, in which the ratio of the isocyanate groups of component (A) to the epoxide groups of the (B) component is comprised within the range of from 99:1 to 50:50.

7. Liquid reactive compositions according to claim 6, in which the ratio of the isocyanate groups of component (A) to the epoxide groups of the (B) component is comprised within the range of from 95:5 to 55:45.

8. Liquid reactive compositions according to claim 1, in which at least one of components (A) and (B) and their mixture, are liquid at temperatures lower than 60° C.

9. Liquid reactive compositions according to claim 1, in which the component (C) is contained in amounts comprised within the range of from 0.01 to 10 parts by weight of halogen X per each 100 parts by weight of (A)/(B) mixture.

10. Liquid reactive compositions according to claim 9, in which the component (C) is contained in amounts comprised within the range of from 0.1 to 4 parts by weight of halogen X per each 100 parts by weight of (A)/(B) mixture.

11. Liquid reactive compositions according to claim 1, in which a fourth component is additionally contained, which is selected from among mineral fillers, short or ground fibres, pigments, extenders, stabilizers, flame-retardant agents, agents endowing the compositions with a thixotropic character, lubricants, mould-release agents, antifoaming agents, propellants, foaming agents, surfactants, wetting agents or other possible known additives or auxiliaries.

* * * * *